United States Patent [19]

Fernando Del Corral et al.

[11] Patent Number: 5,162,354
[45] Date of Patent: Nov. 10, 1992

[54] 3-HALO-5-HALOMETHYL-2-OXAZOLIDINONES AND THEIR USE AS MICROBICIDES

[75] Inventors: Luis Fernando Del Corral, Memphis; S. Rao Rayudu; Marilyn Whittemore, both of Germantown, all of Tenn.

[73] Assignee: Buckman Laboratories International, Inc., Memphis, Tenn.

[21] Appl. No.: 811,147

[22] Filed: Dec. 20, 1991

[51] Int. Cl.$^5$ .................... C07D 263/36; A61K 31/42
[52] U.S. Cl. ........................ 514/376; 106/18.32; 252/49.3; 252/49.5; 422/37; 427/440; 548/229; 548/240; 71/67
[58] Field of Search .................. 514/376; 548/230

[56] References Cited

U.S. PATENT DOCUMENTS

| | | |
|---|---|---|
| 2,881,070 | 7/1959 | Pera . |
| 3,591,601 | 7/1971 | Walles ............... 548/230 |
| 4,000,293 | 12/1976 | Kaminski et al. ........... 514/376 |
| 4,009,178 | 2/1977 | Bodor ............... 548/230 |
| 4,659,484 | 4/1987 | Worley et al. .......... 210/765 |
| 4,681,948 | 7/1987 | Worley ............... 548/319 |
| 4,945,109 | 7/1990 | Rayudu ............... 514/478 |
| 4,954,151 | 9/1990 | Chang et al. . |
| 4,954,156 | 9/1990 | Gautney et al. ........... 71/28 |

FOREIGN PATENT DOCUMENTS

| | | |
|---|---|---|
| 0029579 | 3/1981 | Japan ............... 548/229 |
| 2167405 | 5/1986 | United Kingdom ........ 514/376 |

*Primary Examiner*—Donald G. Daus
*Attorney, Agent, or Firm*—Finnegan, Henderson, Farabow, Garrett & Dunner

[57] ABSTRACT

A 3-halo-5-halomethyl-2-oxazolidinone, a method of making the same and a method of using the compound as a microbicide and for controlling the growth of at least one microorganism in an aqueous system or on a surface. A process for making 5-halomethyl-2-oxazolidinone utilizing an alkali cyanate and an epihalohydrin.

19 Claims, No Drawings

3-HALO-5-HALOMETHYL-2-OXAZOLIDINONES AND THEIR USE AS MICROBICIDES

BACKGROUND OF THE INVENTION

1. Field of the Invention

The present invention relates to novel 3-halo-5-halomethyl-2-oxazolidinones and to the method of their preparation. This invention also relates to methods of use of these compounds as microbicides.

2. Discussion of the Related Art

A large number of commercial, industrial, agricultural, and wood products are subject to microbiological attack which reduces or destroys their economic value. Examples of materials that may be subject to microbiological degradation are surface coatings, wood, agricultural seed, leather and plastics, including flexible plastics.

The temperature at which these products are stored and their intrinsic characteristics make these products susceptible to the growth of microorganisms. These microorganisms can be introduced during the manufacturing of these products by exposure to air, tanks, pipes, equipment, and humans and/or during their use from multiple openings and reclosures of packaged products and by the introduction of contaminated objects to stir or remove material.

Aqueous systems containing organic materials are also highly subject to microbiological attack. Such aqueous systems include latexes, surfactants, dispersants, stabilizers, thickeners, adhesives, starches, waxes, proteins, emulsifying agents, detergents, cellulose products, agricultural irrigation fluids, and resins formulated in aqueous solutions, emulsions or suspensions.

These systems frequently contain relatively large amounts of water causing them to be well-suited environments for microbiological growth and, thus, attack and degradation. Microbiological degradation of aqueous systems containing organic materials may manifest itself as a variety of problems, such as loss of viscosity, gas formation, objectionable odors, decreased pH, emulsion breaking, color change, and gelling.

Another objectionable phenomenon occurring in industrial process systems involving water is slime formation. Slime consists of matted deposits of microorganisms, fibers and debris. It may be stringy, pasty, rubbery, tapioca-like, or hard, and may have a characteristic undesirable odor that is different from that of the liquid suspensions in which it is formed.

The microorganisms primarily involved in slime formation are different species of spore-forming and non-spore-forming bacteria, in particular capsulated forms of bacteria which secrete gelatinous substances that envelop or encase the cells. Slime microorganisms also include filamentous bacteria, filamentous fungi of the mold type, yeasts, and yeast-like organisms. Slime reduces yields in paper production and causes plugging and other problems in water systems.

In addition, different types of water both potable and nonpotable need disinfectants to keep them from being spoiled by microorganisms. In the United States, the most common method of disinfection is the use of chlorination.

Chlorination, however, can be accompanied by some disadvantages, such as chlorine gas explosion or leakage, during water treatment, and may result in the formation of toxic halocarbons, such as chloroform and others In this respect, a variety of compounds are used as replacements for chlorine treatment, including ozone, chlorine dioxide, bromine, potassium permanganate, p-chlorosulfamidobenzoic acid, cyanuric acid derivatives, isocyanuric acid derivatives, quaternary ammonium compounds, and various chloramine compounds, such as 3-chloro-4,4-dimethyl-2-oxazolidinone, which are disclosed in U.S. Pat. No. 4,000,293.

Substituted oxazolidinones containing N-halogen are known compounds. They are described in U.S. Pat. Nos. 3,591,601; 4,000,293, 4,659,484 and 4,954,151 as well as other patents and literature. To the inventors' knowledge, 3-halo-5-halomethyl-2-oxazolidinones are not known in the art.

Walles, in U.S. Pat. No. 3,591,601, describes compounds of the general formula:

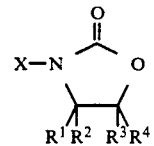

where $R^1$, $R^2$, $R^3$ and $R^4$ can be lower alkyl or hydrogen and X can be either bromine or chlorine. Kaminski, in U.S. Pat. No. 4,000,293, specifically includes compounds where $R^1$ and $R^2$ are lower alkyl groups and $R_3$ and $R_4$ are hydrogens or $R^1$ and $R^2$ are hydrogens and $R^3$ and $R^4$ are lower alkyl groups. Kaminski claims that it is essential for these compounds to have either a 4- or 5-quaternary carbon to be useful as disinfectants (Col. 2, lines 54–58).

Most of the researchers in this field consider that germinal alkyl groups are required for the use of N-Halo oxazolidinones as disinfectants. However, the present inventors have surprisingly found that 3-halo-2-oxazolidinones having a halomethyl substituent at the 5-position can provide long term disinfectant effectiveness.

As can be seen in the description provided above of the known compounds, neither of the above patents disclosed or suggested either the preparation or use of 3-halo-5-halomethyl-2-oxazolidinones. As is described below, particularly in Examples 1 and 2, these compounds can be prepared from readily available starting materials. In addition, the 5-halomethyl group in these compounds can provide an additional source of halogen for additional and lasting disinfectant activity of these compounds.

SUMMARY OF THE INVENTION

It is an object of the invention to provide novel 3-halo-5-halomethyl-2-oxazolidinones which can be used as microbicides and disinfectants.

A second object is to provide a method for the preparation of 5-halomethyl-2-oxazolidinones and 3-halo-5-halomethyl-2-oxazolidinones.

A third object of the invention is to provide a method for inhibiting the growth of microorganisms in aqueous systems using 3-halo-5-halomethyl-2-oxazolidinones.

A fourth object of this invention is to provide a method for sanitizing hard surfaces using a 3-halo-5-halomethyl-2-oxazolidinone.

These objects can be accomplished at least in part by a 3-halo-5-halomethyl-2-oxazolidinone compound of formula I:

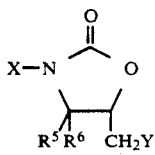

wherein X is Cl or Br; Y is Cl or Br; $R^5$ is hydrogen or lower alkyl; and $R^6$ is hydrogen or lower alkyl.

Preferred compounds of the formula I include 3-Bromo-5-chloromethyl-2-oxazolidinone, 3-Chloro-5-chloromethyl-2-oxazolidinone, 3-Bromo-5-bromomethyl-2-oxazolidinone, and 3-Chloro-5-bromomethyl-2-oxazolidinone.

The invention also relates to a microbicide comprising an effective amount of the compound of formula I as well as to a method for the control of at least one microorganism in an aqueous system comprising adding to an aqueous system an effective amount of the compound of formula I, and to a method of controlling the growth of at least one microorganism on a surface comprising treating a surface with an effective amount of the compound of formula I.

The invention also relates to a method for the preparation of a 3-halo-5-halomethyl-2-oxazolidinone compound comprising the steps of reacting an alkali cyanate with an epihalohydrin for a time sufficient to form 5-halomethyl-2-oxazolidinone and then halogenating said 5-halomethyl-2-oxazolidinone for a time sufficient to form said 3-halo-5-halomethyl-2-oxazolidinone.

The invention also relates to a method for the preparation of a 5-halomethyl-2-oxazolidinone compound comprising the step of reacting an alkali cyanate with an epihalohydrin for a time sufficient to form said 5-halomethyl-2-oxazolidinone.

Additional objects and advantages of this invention will be set forth in the description which follows, and in part will be apparent from the description, or may be learned by the practice of this invention.

DETAILED DESCRIPTION OF THE INVENTION 3-halo-5-halomethyl-2-oxazolidinones of the present invention can be represented by the general formula I:

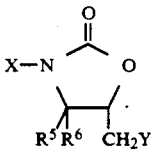

where $R^5$ and $R^6$ are independently either lower alkyl, preferably $C_1$-$C_{10}$ alkyl, or hydrogen, X is bromine or chlorine and Y is bromine or chlorine The synthesis of compounds according to formula I can be carried out by reacting an alkali cyanate with an appropriately substituted epihalohydrin, preferably in the presence of magnesium sulfate, more preferably in the presence of $MgSO_4.7H_2O$, followed by halogenating the product of that reaction to obtain the desired compound described above. The role of the magnesium sulfate is to salt out the desired organic product. All of the reagents needed are readily available commercially or can be routinely synthesized.

Alkali cyanates such as sodium or potassium cyanate can be used in the synthesis of compounds of formula I.

Potassium cyanate is generally more soluble and is preferred. Illustrative epihalohydrins which can be used to synthesize compounds of formula I include epichlorohydrin and epibromohydrin as well as substituted epihalohydrins such as 3-(chloromethyl-)-2,2-dimethyl oxirane, 3-(chloromethyl)-2-methyl-2-pentyl oxirane and 3-(chloromethyl)-2-octyl oxirane.

Illustrative methods of halogenation include he use of bromine in the presence of a base to achieve bromination and the use of trichloroisocyanuric acid to achieve chlorinmation.

The reaction of an alkali cyanate with an appropriate epihalohydrin to form a 5-halomethyl-2-oxazolidinone intermediate is conducted for a time sufficient and at a temperature sufficient to obtain the desired intermediate. Reaction times preferably range from 2 to 4 hours, more preferably from 2 to 3 hours, and reaction temperatures preferably range from 70° to 100° C., more preferably from 90° to 95° C. when a 5-chloromethyl compound is being prepared and about 75 ° C. when a 5-bromomethyl compound is being prepared.

The molar ratio of alkali cyanate to ipihalohydrin preferably ranges from 2:1 to 1:1, more preferably about 2:1. When magnesium sulfate is present int he reaction, the molar ratio of alkali cyanate to magnesium sulfate preferably ranges from 1:1 to 3:1, more preferably about 1:1.

With respect to the halogenation step, halogenation is carried out for a time end at a temperature sufficient to obtain the desired 3-halo-5-halomthyl-2-oxazolidinone. For example, to achieve bromination, a preferred temperature ranges from 0° to 25° C., more preferably from 0° C. to 5° C. Chlorination is preferably carried out at a temperature ranging from 0° C. to 30° C., more preferably at room temperature. Reaction times preferably range from 15 to 120 minutes.

In affecting halogenation, the molar ratio of halogen or source of halogen to 5-halomethyl-2-oxazolidinone preferably ranges from 1:1 to 1.5:1, more preferably about 1:1.

The invention also relates to a microbicide comprising an effective amount of a compound of formula I. The compounds of formula I are also useful in a method for the control of at least one microorganism in an aqueous system comprising adding to an aqueous system an effective amount of a compound of formula I, and in a method of controlling the growth of at least one microorganism on a surface comprising treating a surface with an effective amount of a compound of formula I. Illustrative aqueous systems and material surfaces which are subject to microbiological attack or degradation and which can be treated with compounds of formula I are discussed above in the Description of Related Art.

The particular effective amounts will depend on the microorganism and the medium being treated as shown by the examples below. The compound of formula I may be added as a concentrate to a medium to be treated or can be diluted before use.

The following examples are given to illustrate the invention. It should be understood, however, that the invention is not to be limited to the specific conditions or details set forth in these examples.

EXAMPLE 1

Preparation of 5-Chloromethyl-2-oxazolidinone 40.56 grams (0.50 moles) potassium cyanate were dissolved in 200 mL water and added to 123.24 grams (0.50 moles) $MgSO_4.7H_2O$ dissolved in 200 mL water in a three-neck flask equipped with condenser, mechanical stirrer, addition funnel and thermometer. The reaction mixture was heated at 65° C before the addition of 23.13 grams (0.25 moles) epichlorohydrin was begun by means of an addition funnel. The best yield was achieved when the epichlorohydrin addition was completed before the temperature rose above 80°–85° C. The reaction temperature was then maintained at 90°–95° C. for 1 to 2 hours. After the reaction mixture cooled, the mixture was added to a separatory funnel and extracted with three 50 mL portions of ethyl acetate. These fractions were combined and dried over magnesium sulfate before removing the solvent with a rotary evaporator to recover a white crystalline product, with melting point of 106° C. Yield is 33.8 grams (35% yield). Proton NMR Data: $\delta 3.15$ (t, 1 proton), 3.5 (t, 1 proton), 3.75 (dq, 2 protons) 4.7 (m, 1 proton), 7.5 (s, 1 proton).

EXAMPLE 2

Preparation of 5-Bromomethyl-2-oxazolidinone 60.2 grams (0.72 moles) KOCN were dissolved in 125 mL water and added to 178 grams (0.73 moles) $MgSO_4.7H_2O$ dissolved in 12.5 mL water. The mixture was heated to 60° C. before the addition of 50 grams (0.37 moles) epibromohydrin was begun. The temperature was 75° C. and heating was continued for two hours. After cooling, the mixture was extracted with ethyl acetate, dried and the solvent removed by rotary evaporation to yield 18.3 grams crystals (28.5% yield) with melting point of 102°–103° C.

EXAMPLE 3

Preparation of 3-Bromo-5-chloromethyl-2-oxazolidinone (Compound 1)

13.55 grams (0.1 mole) 5-chloromethyl-2-oxazolidinone, prepared in Example 1, were dissolved in 90 mL of a 1 M NaOH solution and then cooled to 0° C. 17.6 grams (0.11 moles) bromine were added dropwise, with stirring over a period of fifteen minutes. The product was extracted with methylene chloride. The extracts were then combined, dried and the solvent removed using a rotary evaporator to yield an orange solid. Proton NMR Data: $\delta 3.15$ (m, 1 proton), 3.48 (m, 1 proton), 3.7 (m, 2 protons), 4.7 (m, 1 proton) Elemental Analysis: Found (theory), C 24.05 (22.40), H 2.71 (2.35), N 6.98 (6.53), Cl 18.12 (16.53), Br 31.18 (37.26).

EXAMPLE 4

Preparation of 3-Chloro-5-chloromethyl-2-oxazolidinone (Compound 2)

8.4 grams (0.036 moles) trichloroisocyanuric acid were dissolved in dried methylene chloride. To this suspension were added 5 grams (0.036 moles) 5-Chloromethyl-2-oxazolidinone. The mixture was stirred for several hours before filtering to remove solids. The methylene chloride layer was rotovaped to recover the product, a yellow liquid Proton NMR Data: $\delta 3.7$ (m, 4 protons), 4.8(m, 1 proton). Elemental analysis Chlorine found 39.66 (theory 41.7).

EXAMPLE 5

Preparation of 3-Bromo-5-bromomethyl-2-oxazolidinone (Compound 3)

2.67 grams (0.0166 moles) bromine were added to 3 grams (0.0166 moles) 5-bromomethyl-2-oxazolidinone and the reaction mixture was chilled to 0°–5° C. with stirring. Chilled 50% potassium hydroxide was added slowly until the red $Br_2$ color disappeared. Proton NMR Data: $\delta 3.7$(m, 4 protons), 5.1(m, 1 proton) Elemental analysis Bromine 60.43 Theory 61.8.

EXAMPLE 6

Preparation of 3-Chloro-5-bromomethyl-2-oxazolidinone (Compound 4)

3.86 grams (0.0166 moles) trichlorocyanuric acid and 1.79 grams (0.0166 moles) 5-bromomethyl-2-oxazolidinone are added to $MeCl_2$ and stirred overnight at room temperature. The reaction mix was dried over magnesium sulfate and rotovaped. Proton NMR Data: $\delta 3.9$(m, 4 protons]5.1(m, 1 proton).

EXAMPLE 7

Compounds 1–4 of Examples 3–6 of the present invention were tested by the basal salts method described in U.S. Pat. No. 2,881,070 at column 5, beginning at line 12 and extending to column 6, line 53. The disclosure of U.S. Pat. No. 2,881,070 is specifically incorporated by reference herein As set forth therein, a percentage kill of 80% or higher represents an extremely useful microbicidal composition, but it does not follow that higher kills are necessarily better or more desirable. The minimum inhibitory concentrations are those in which a percentage kill of at least 80% is obtained. The results are presented in TABLE I.

TABLE I

| Minimum inhibitory concentrations against *Enterobacter aerogenes* in parts per million (w/v). | | |
|---|---|---|
| Compound # | pH 6.0 | pH 8.0 |
| 1 | 10 | 10 |
| 2 | 8 | 10 |
| 3 | 2 | 4 |
| 4 | 10 | 20 |

EXAMPLE 8

The microorganism growth inhibiting activity of compounds 1–4 on the fungus *Aspergillus niger* was evaluated. The method is described in U.S. Pat. No. 4,945,109, column 5 beginning at line 47 to column 6, line 33. The disclosure of U.S. Pat. No. 4,945,109 is incorporated herein by reference. The minimum inhibitory concentrations are those that completely prevented the growth of fungi. The results are Presented in Table II.

TABLE II

| Minimum inhibitory concentration of the compounds against fungi in parts per million (w/v). | |
|---|---|
| Compound # | *Aspergillus niger* pH 6.0 |
| 1 | 10 |
| 2 | 128 |
| 3 | 100 |

TABLE II-continued

Minimum inhibitory concentration of the compounds against fungi in parts per million (w/v).

| Compound # | Aspergillus niger pH 6.0 |
|---|---|
| 4 | 100 |

EXAMPLE 9

The growth inhibiting activity of the method of the invention against the three algae *Chlorella pyrenoidosa, Chlorococcum hypnosporum* and *Phormidium inundatum* was evaluated in Difco Algae Broth, the content of which was as follows:

| Compound | Grams Per liter |
|---|---|
| Sodium nitrate | 1.000 |
| Ammonium chloride | 0.050 |
| Calcium chloride | 0.058 |
| Magnesium sulfate | 0.513 |
| Dipotassium phosphate | 0.250 |
| Ferric chloride | 0.003 |

Forty-gram portions of the algae medium were added to 250 mL Pyrex Erlenmeyer flasks fitted with loose metal caps and then sterilized. Each of the following substances was then added to the flasks in the order listed:

1. Sterile algae medium as required to bring the total weight of the contents of each flask to 50 grams, after allowing for all subsequent additions specified below.
2. A solution of one of compounds 1-4 or of a control agent to be evaluated in each test, to give the concentration desired in parts per million by weight.
3. *Chlorella pyrenoidosa, Chlorococcum hypnosporum* and *Phormidium inundatum* in amounts sufficient to give excellent growth in the controls after 14 days. This was achieved by adding 1 milliliter of a 14 day old culture having luxuriant growth. The *Chlorella pyrenoidosa* culture was obtained from American Type Culture Collection No. 7516; *Chlorococcum hypnosporum*, from the University of TX at Austin; and *Phormidium inundatum*, WI No. 1093, from the University of WA.

As a control experiment, WSCP was used as a positive control agent. WSCP is a known toxicant which kills *C. pyrenoidosa* at 2 ppm, *C. hypnosporum* at 2ppm, and *P. inundatum* at 10 ppm. Control experiments were also carried out where no toxicants were employed. In the algicidal tests, the growth of algae in the nutrient medium is lush green and can be seen with the naked eye. Because the minimum inhibitory concentrations of the compounds in this example are those which result in complete inhibition, evaluation of the test results is not subjective.

After the inoculum of the test algae was added, the flasks were incubated at a temperature of 28°±2° C. under fluorescent illumination of 250 foot-candle intensity (8 hours light, 16 hours darkness) for a period adequate for growth in the controls (those portions of medium which contained no toxicant). Observations of growth were made at 7-day intervals. Minimum inhibitory concentrations are those that prevented complete growth after 28 days. The results are summarized in Table III.

TABLE III

Minimum inhibitory concentration of the compounds against algae in parts per million (w/v).

| Compound # | C. pyrenoidosa pH 7 | C. hypnosporum pH 7 | P. inundatum pH 7 |
|---|---|---|---|
| 1 | 10 | 10 | 2.0 |
| 2 | 1.0 | 1.0 | 1.0 |
| 3 | 2 | 8 | 2 |
| 4 | 4 | 8 | 8 |

EXAMPLE 10

AOAC Disinfectant Swimming Pool Assay

This example was based on the procedure described in AOAC (Association of Official Analytical Chemists) Official Methods of Analysis (1986) pp 75-77. The results obtained by this method are suitable for presumptive evidence of acceptability of products for disinfecting swimming pool water. The results obtained for Compound 1 in a contact time of 10 minutes are noted in Table IV.

TABLE IV

Minimum inhibitory concentration of Compound 1 required to inhibit microorganisms in parts per million (w/v).

| Microorganism | MIC (in ppm) |
|---|---|
| *Escherichia coli* | 80 |
| *Salmonella choleraesuis* | 80 |
| *Streptococcus faecalis* | 80 |
| *Pseudomonas aeruginosa* | 100 |
| *Klebsiella pneumonia* | 100 |

EXAMPLE 11

AOAC Germicidal and Detergent Sanitizing Action of Disinfectants

This test is conducted according to AOAC methods described in AOAC Official Methods of Analysis (1984) p 70. This test is suitable for chemicals that can be permitted for use in sanitizing precleaned non-porous food contact surfaces. This test also determines the effectiveness of compounds tested in hard water. Most of the detergents/sanitizers available in the market become ineffective in the presence of hard water, i.e. water containing calcium and/or magnesium ions. A water hardness value of 400 ppm was chosen because it is considered to be the highest hardness value for tap water in the United States. The results of tests conducted in this way against different microorganisms are listed in Table V.

TABLE V

Minimum inhibitory concentration of Compound 1 required to inhibit microorganisms in parts per million (w/v).

| Microorganism | Soft Water | Hard Water (400 ppm)[1] |
|---|---|---|
| *Escherichia coli* | 80 | 80 |
| *Streptococcus faecalis* | 80 | 80 |

[1](calcium carbonate)

EXAMPLE 12

Efficacy of Sanitizers Recommended for Non-Food Contact Surfaces

This test method is used to evaluate the antimicrobial efficacy of sanitizers on precleaned non-porous, non-food contact surfaces. This test was performed according to the test procedure E 1153-87 of ASTM. Under this method, a concentration that can reduce the original population to 0.1% (99.9% kill) is considered to be an effective concentration for use as a sanitizer. For most of the sanitizers, effectiveness is hampered (or minimum inhibitory concentrations go up) in the presence of an organic load. Therefore, the compounds of the present invention are tested both in the presence and absence of 5% organic load (Bovine albumin fraction V, Sigma Chemical Company). The results are listed in Table VI.

TABLE VI

Minimum inhibitory concentration of Compound 1 required to inhibit microorganisms in parts per million (w/v).

| Microorganism | Without organic load | With 5% organic load |
|---|---|---|
| Staphylococcus aureus | 80 | 160 |
| Escherichia coli | 80 | 160 |

EXAMPLE 13

Long-Term Effectiveness of Compounds in water as Disinfectants

In order to test the effectiveness of the compounds of the present invention over a period of 15 days, the following experiment was conducted using Compound 1.

The basal salts method described in U.S. Pat. No. 2,881,070 at column 5, beginning at line 12 and extending to column 6, line 53 was performed at two different pH values and percent kills were obtained with a mixture of test organisms (*Staphylococcus aureus, Enterobacter aerogenes and Pseudomonas aeruginosa*). The results obtained for Compound 1 are shown in Table VII. As can be observed 99.99% or greater activity is maintained up to three days post-preparation in water for short contact sanitizing (up to 10 min) exposure at pH 6 and 99.96% or greater activity is maintained up to three days post-preparation in water for the short contact sanitizing exposure at pH 8. At 80 ppm, prolonged sanitizing ability is maintained (99% or greater) with prolonged exposure times (24 hours contact through 15 ways post-preparation in water).

TABLE VII

Long-Term Efficacy of Compound 1 against mixture of *Staphylococcus aureus, Enterobacter aerogenes* and *Pseudomonas aeruginosa*

| Days after preparation in Soft Water | Conc. in ppm | pH | % Reduction (Kill) 10 min contact | 24 hours contact |
|---|---|---|---|---|
| Day 1 | Control[a] | 6.0 | $1.26 \times 10^7$ | — |
|  | 40 | 6.0 | 99.99 | 100 |
|  | 80 | 6.0 | 99.99 | 100 |
|  | Control[a] | 8.0 | $1.17 \times 10^7$ | — |
|  | 40 | 8.0 | 100 | 100 |
|  | 80 | 8.0 | 100 | 100 |
| Day 2 | Control[a] | 6.0 | $1.35 \times 10^7$ | $3.5 \times 10^7$ |
|  | 40 | 6.0 | 100 | 100 |
|  | 80 | 6.0 | 100 | 100 |
|  | Control[a] | 8.0 | $1.41 \times 10^7$ | $3.76 \times 10^7$ |
|  | 40 | 8.0 | 99.99 | 100 |
|  | 80 | 8.0 | 99.99 | 99.999 |
| Day 3 | Control[a] | 6.0 | $1.38 \times 10^7$ | $1.80 \times 10^7$ |
|  | 40 | 6.0 | 99.99 | 100 |
|  | 80 | 6.0 | 99.999 | 100 |
|  | Control[a] | 8.0 | $1.41 \times 10^7$ | $3.20 \times 10^7$ |
|  | 40 | 8.0 | 99.96 | 100 |
|  | 80 | 8.0 | 99.96 | 100 |
| Day 4 | Control[a] | 6.0 | $1.96 \times 10^7$ | $5.0 \times 10^7$ |
|  | 40 | 6.0 | 38.8 | 99.6 |
|  | 80 | 6.0 | 54.3 | 99.9 |
|  | Control[a] | 8.0 | $1.63 \times 10^7$ | $1.99 \times 10^7$ |
|  | 40 | 8.0 | 34.2 | 98.7 |

TABLE VII-continued

Long-Term Efficacy of Compound 1 against mixture of *Staphylococcus aureus, Enterobacter aerogenes* and *Pseudomonas aeruginosa*

| Days after preparation in Soft Water | Conc. in ppm | pH | % Reduction (Kill) 10 min contact | 24 hours contact |
|---|---|---|---|---|
|  | 80 | 8.0 | 46.0 | 99.96 |
| Day 5 | Control[a] | 6.0 | $1.42 \times 10^7$ | $5.60 \times 10^7$ |
|  | 40 | 6.0 | 26.8 | 91.8 |
|  | 80 | 6.0 | 41.4 | 99.57 |
|  | Control[a] | 8.0 | $1.18 \times 10^7$ | $1.75 \times 10^7$ |
|  | 40 | 8.0 | 51.8 | 99.93 |
|  | 80 | 8.0 | 51.8 | 99.92 |
| Day 14 | Control[a] | 6.0 | $2.47 \times 10^7$ | $5.68 \times 10^7$ |
|  | 40 | 6.0 | 40.0 | 99.78 |
|  | 80 | 6.0 | 28.7 | 99.99 |
|  | Control[a] | 8.0 | $1.15 \times 10^7$ | $2.72 \times 10^7$ |
|  | 40 | 8.0 | 69.5 | 99.5 |
|  | 80 | 8.0 | 83.8 | 99.9 |
| Day 15 | Control[a] | 6.0 | $2.44 \times 10^7$ | — |
|  | 40 | 6.0 | 39.34 | 96.0 |
|  | 80 | 6.0 | 13.11 | 99.97 |
|  | Control[a] | 8.0 | $1.81 \times 10^7$ | — |
|  | 40 | 8.0 | 68.6 | 99.3 |
|  | 80 | 8.0 | 70.2 | 99.96 |

[a]Control indicates the population of the test organism and is used to make sure there is vigorous growth and to calculate % kills.

The claimed invention is:

1. A 3-halo-5-halomethyl-2-oxazolidinone compound of formula (I)

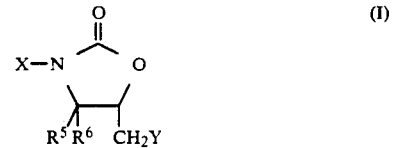

wherein
X is Cl or Br;
Y is Cl or Br;
$R^5$ is hydrogen or lower alkyl; and
$R^6$ is hydrogen or lower alkyl.

2. The compound of claim 1 wherein the compound is 3-bromo-5-chloromethyl-2-oxazolidinone.

3. The compound of claim 1 wherein the compound is 3-chloro-5-chloromethyl-2-oxazolidinone.

4. The compound of claim 1 wherein the compound is 3-bromo-5-bromomethyl-2-oxazolidinone.

5. The compound of claim 1 wherein the compound is 3-chloro-5-bromomethyl-2-oxazolidinone.

6. A method for the preparation of a 3-halo-5-halomethyl-2-oxazolidinone compound comprising the steps of reacting an alkali halomethyl-2-oxazolidinone and then halogenating said 5-halomethyl-2-oxazolidinone for a time sufficient to form said 3-halo-5-halomethyl-2-oxazolidinone.

7. The method of claim 6 wherein the epihalohydrin is selected from epichlorohydrin and epibromohydrin and the alkali cyanate is potassium cyanate.

8. The method of claim 7 wherein the reaction is carried out in the presence of $MgSO_4$ or $MgSO_4.7H_2O$.

9. A microbicide comprising a microbiocidally effective amount of a compound of formula I of claim 1.

10. A microbicide comprising a microbiocidally effective amount of the compound of claim 2.

11. A microbicide comprising a microbiocidally effective amount of the compound of claim 3.

12. A microbicide comprising a microbiocidally effective amount of the compound of claim 4.

13. A microbicide comprising a microbiocidally effective amount of the compound of claim 5.

14. A method for the control of at least one microorganism in an aqueous system comprising adding to an aqueous system an amount of a compound of formula I of claim 1 effective to control said microorganism.

15. The method of claim 14 wherein the aqueous system is a metal working fluid, an agricultural irrigation fluid or a swimming pool.

16. The method of claim 15 wherein the compound of formula I is selected from 3-Bromo-5-chloromethyl-2-oxazolidinone, 3-Chloro-5-chloromethyl-2-oxazolidinone, 3-Bromo-5-bromomethyl-2-oxazolidinone, or 3-Chloro-5-bromomethyl-2-oxazolidinone.

17. A method of controlling the growth of at least one microorganism on a surface comprising treating a surface with an amount of a compound of claim 1 effective to control said microorganism.

18. The method of claim 17 wherein the surface is a surface of a coating, a wood surface, an agricultural seed surface, a leather surface or a plastic surface.

19. The method of claim 18 wherein the compound of formula I is selected from 3-Bromo-5-chloromethyl-2-oxazolidinone, 3-Chloro-5-chloromethyl-2-oxazolidinone, 3-Bromo-5-bromomethyl-2-oxazolidinone, or 3-Chloro-5-bromomethyl-2-oxazolidinone.

* * * * *

UNITED STATES PATENT AND TRADEMARK OFFICE
CERTIFICATE OF CORRECTION

PATENT NO. : 5,162,354
DATED : November 10, 1992
INVENTOR(S) : Fernando Del Corral et al.

It is certified that error appears in the above-identified patent and that said Letters Patent is hereby corrected as shown below:

Column 10, line 52, cancel beginning with "6. A method for" to and including "halomethyl-2-oxazolidinone." in column 10, line 57, and insert the following claim:

6.  A method for the preparation of a 3-halo-5-halomethyl-2-oxazolidinone compound comprising the steps of reacting an alkali cyanate with an epihalohydrin for a time sufficient to form 5-halomethyl-2-oxazolidinone and then halogenating said 5-halomethyl-2-oxazolidinone for a time sufficient to form said 3-halo-5-halomethyl-2-oxazolidinone.

Signed and Sealed this

Ninth Day of November, 1993

Attest:

BRUCE LEHMAN

Attesting Officer

Commissioner of Patents and Trademarks